United States Patent
Smith et al.

[11] Patent Number: 5,897,090
[45] Date of Patent: Apr. 27, 1999

[54] PUCK FOR A SAMPLE TUBE

[75] Inventors: Gary Thomas Smith, Collegeville; David Patrick O'Bryan, Kennett Square; Bingham Hood Van Dyke, Gilbertsville, all of Pa.; Michael John Campanelli, Mahopac, N.Y.

[73] Assignee: Bayer Corporation, Tarrytown, N.Y.

[21] Appl. No.: 08/969,510

[22] Filed: Nov. 13, 1997

[51] Int. Cl.⁶ ............................................. A47K 1/08
[52] U.S. Cl. .................... 248/311.2; 206/306; 248/314
[58] Field of Search ........................ 248/311.2, 314, 248/316.3; 206/306; 215/DIG. 1; 220/529, 737

[56] References Cited

U.S. PATENT DOCUMENTS

| | | | |
|---|---|---|---|
| D. 42,197 | 2/1912 | Eustis | 248/311.2 |
| 143,417 | 10/1873 | Munroe | 248/539 |
| 1,351,007 | 8/1920 | Shephard | 248/524 |
| 2,337,914 | 12/1943 | Meldrum | 248/523 |
| 2,647,712 | 8/1953 | Sandmoen | 248/314 |
| 3,671,004 | 6/1972 | Cram | 248/316.3 |
| 3,918,920 | 11/1975 | Barber | 248/314 |
| 4,729,413 | 3/1988 | Shults | 141/2 |
| 5,014,868 | 5/1991 | Wittig et al. | 206/306 |
| 5,484,052 | 1/1996 | Pawloski et al. | 198/803.11 |

Primary Examiner—Leslie A. Braun
Assistant Examiner—Robert Lipcsik
Attorney, Agent, or Firm—Andrew L. Klawitter; Rodman & Rodman

[57] ABSTRACT

The puck for a sample tube includes a housing, a spring device and an end cap. The spring device has an annular base portion and angularly spaced spring arms that extend upwardly from the base portion and then bend downwardly toward the base portion. The end cap includes a hub portion around which the spring device is mounted. The cap with the spring device are fixed at one end of the housing and a portion of the spring arms extend into the interior space of the housing. The downwardly directed portion of the spring arm includes a sample tube engaging portion that is substantially parallel with a central axis of the housing. Thus a sample tube inserted in the puck engages the sample tube engaging portions of the spring arms which exert a biasing force against the sample tube. The spring arms provide an optimum restraining force against the sample tube to permit easy insertion and removal of the sample tube from the puck.

21 Claims, 3 Drawing Sheets

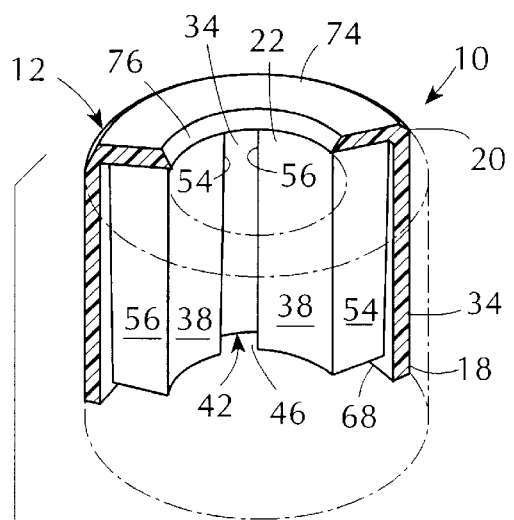
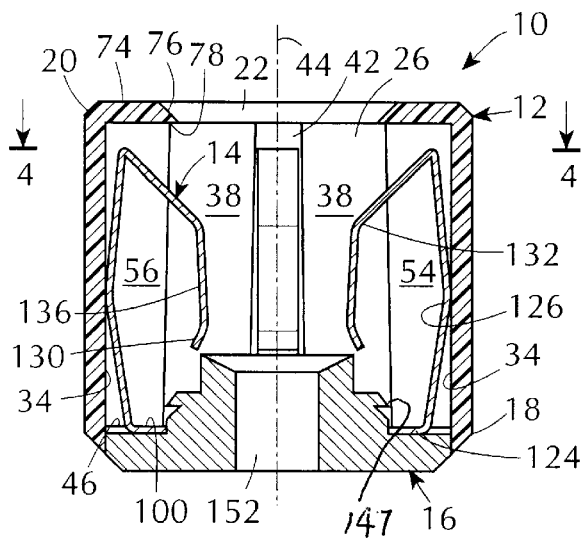
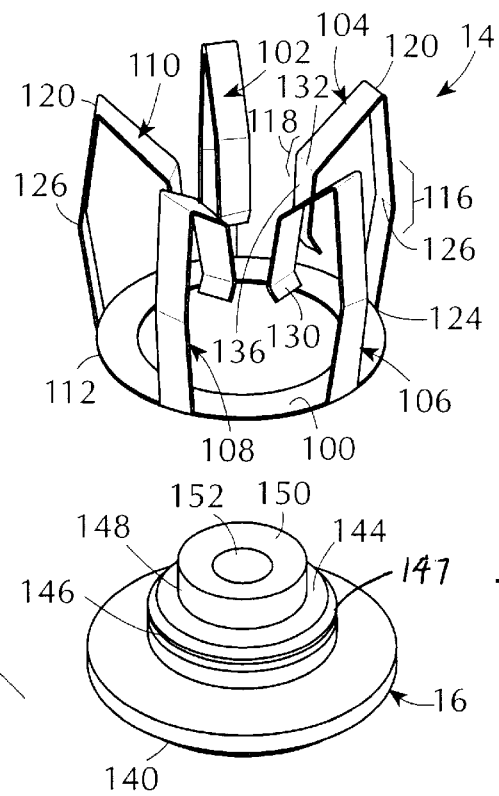
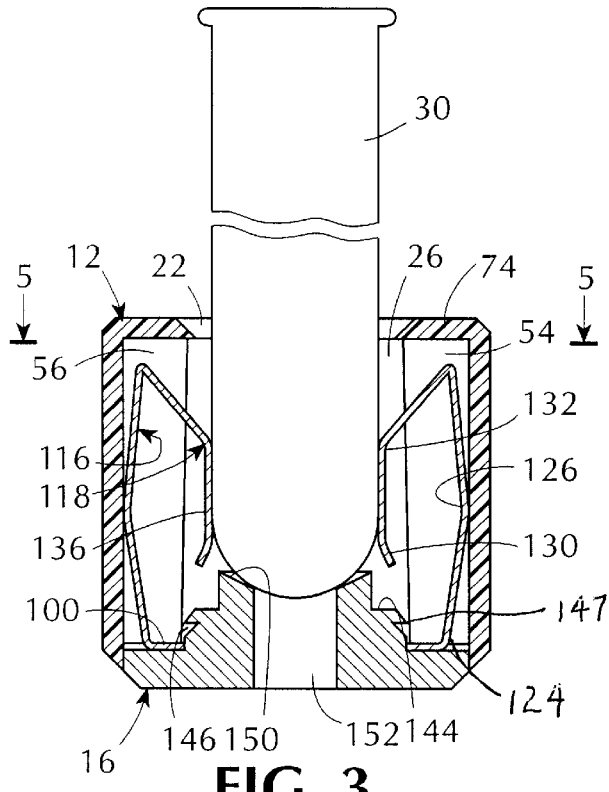

FIG. 7
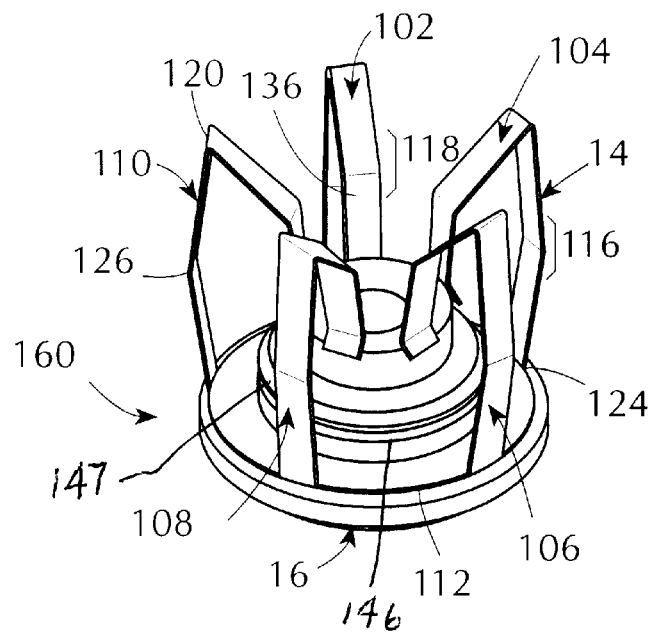
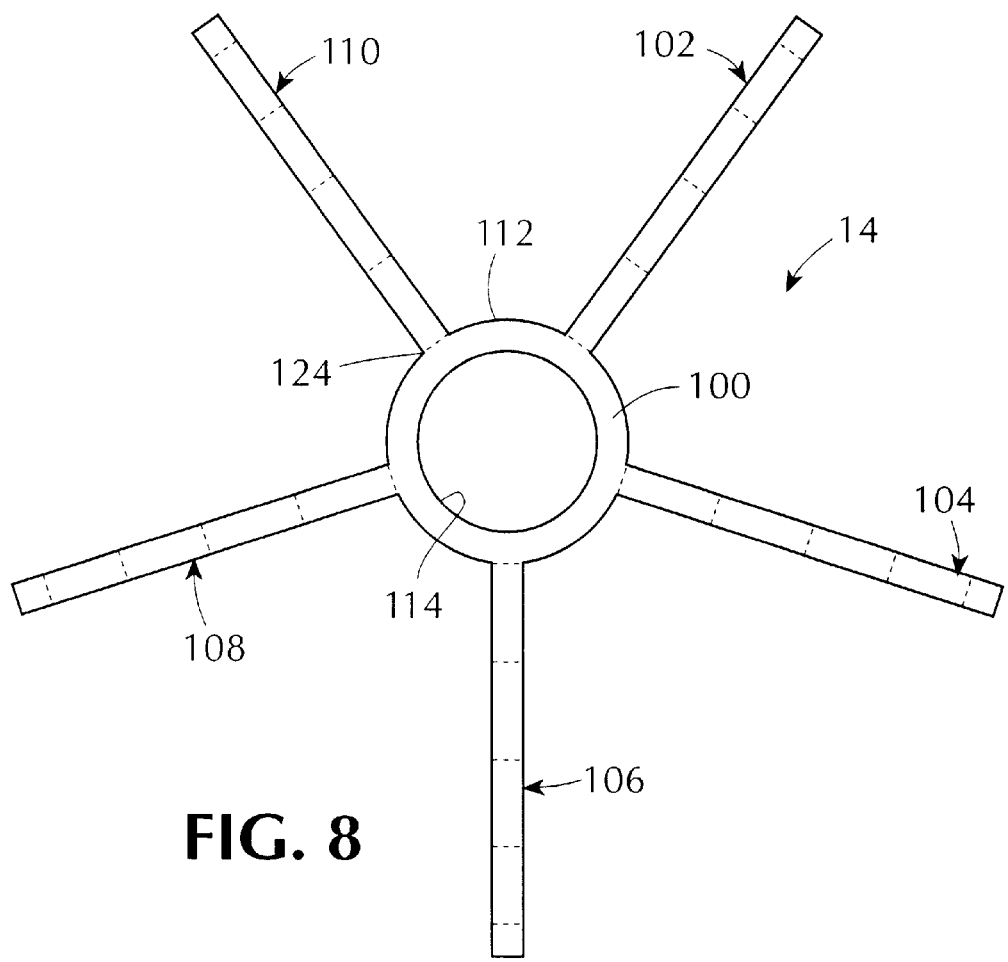
FIG. 8

PUCK FOR A SAMPLE TUBE

BACKGROUND OF THE INVENTION

This invention relates to devices for holding an individual container in an upright position while the container is being transported from one location to another, and more particularly to a novel puck for a sample tube.

Samples of biological materials such as blood, urine or other body fluid that are subject to clinical testing on a massive scale are usually processed in one or more automated apparatus. Various known clinical apparatus can automatically perform such functions as dividing a relatively large sample of body fluid into smaller sized test quantities, mixing a divided sample with an appropriate diluent, and performing a selected test or a series of selected tests on the test sample.

In some instances it has been found convenient to automatically deliver a sample tube from one location to another for diverse processing and/or test purposes. A commonly used transport device for sample tubes is a conveyor.

The sample tube, which usually contains a bar code or other indicia capable of automatic identification, is typically disposed in a carrying device such as a puck that is placed on a conveyor. The puck, which includes a receptacle for the sample tube, is intended to stabilize the tube in an upright position during its journey on the conveyor belt to one or more predetermined destinations corresponding to one or more test apparatus. When the puck is at a test apparatus station the sample tube is usually removed from the puck by an automatic handling device such as a robot, which delivers the sample tube to the test apparatus for testing. The empty puck, which normally remains on the conveyor, is automatically reloaded, by a robot, for example, with another sample tube that has completed the test cycle in the test apparatus.

Since it may be necessary to accomplish rapid removal and insertion of a sample tube in and out of the puck on a frequent basis it is desirable that the puck hold the sample tube with an optimum retaining force that permits easy removal and insertion of the sample tube in and out of the puck.

OBJECTS AND SUMMARY OF THE INVENTION

Among the several objects of the invention may be noted the provision of a novel puck for a sample tube, a novel puck for a sample tube that centers the sample tube in the puck for convenient insertion and removal of the sample tube from the puck, a novel puck for a sample tube that holds the sample tube with an optimum retaining force that permits easy insertion and removal of the sample tube from the puck, a novel puck for a sample tube having a one piece spring device that facilitates construction and assembly of the puck, a novel puck for a sample tube having a novel spring that centers the sample tube within the puck housing, a novel puck for a sample tube with a spring device having spring arms that are deflectable toward and away from the axis of the puck and a novel puck that can accommodate sample tubes of different diameter within a predetermined size range.

Other objects and features of the invention will be in part apparent and in part pointed out hereinafter.

In accordance with the invention the puck includes a generally cylindrical housing having a tube receiving opening at one end to provide access to the interior space of the housing and an end cap at the opposite end of the housing. A spring device is supported on the end cap which locks the spring in the housing. The spring device is preferably a one piece structure and has an annular base portion, with the spring arms extending upwardly from the base portion toward the sample tube receiving opening of the housing. The spring arms are radially spaced around the interior of the housing at substantially equal angles and include radially outer and inner sections with respect to a central axis of the housing. The radially outer sections of the spring arms project upwardly from the end cap toward the tube receiving opening and the radially inner sections of the spring arms are bent over to extend downwardly toward the end cap. The radially inner section of each spring arm includes a sample tube engaging portion that is substantially parallel with the central axis of the housing to engage sample tubes that are disposed within the housing. The sample tube engaging portions are substantially equally spaced from the central axis.

Slots formed in an inner wall of the housing receive the radially outer sections of the spring arms, whereas the radially inner sections of the spring arms are disposed in the interior space of the housing.

The end cap constitutes the base of the puck and provides necessary bottom weight to help keep the puck in an upright position. The end cap includes a hub portion on which the annular base portion of the spring device is mounted. The end cap is pressed into one end of the housing with the annular base portion of the spring device being sandwiched between the end cap and a recessed end portion of the inner wall of the housing.

When a sample tube is disposed in the puck the peripheral surface of the sample tube contacts and deflects the sample tube engaging portion of the spring arm. Selected other portions of the spring arm that do not engage the sample tube are likewise deflectable away from the central axis of the housing in response to insertion of the sample tube. In this manner the deflection of the spring arms provide a biasing force against the sample tube that is sufficient to hold the tube in the housing yet permit easy withdrawal of the tube from the puck when such withdrawal is desired. The sample tube engaging portions of the spring arms also center the tube in the puck.

The invention accordingly comprises the constructions hereinafter described, the scope of the invention being indicated in the claims.

DESCRIPTION OF THE DRAWINGS

In the drawings,

FIG. 2 is a sectional view in elevation of the puck;

FIG. 3 is a view similar to FIG. 2, with the sample tube inserted in the puck;

FIG. 6 is an exploded view of the puck components;

FIG. 7 is a perspective view of the spring device and cap thereof in the form of a subassembly; and, FIG. 8 is a developmental plan view of the spring device.

Corresponding reference characters indicate corresponding parts throughout the several views of the drawings.

DETAILED DESCRIPTION OF THE INVENTION

Figure 1:
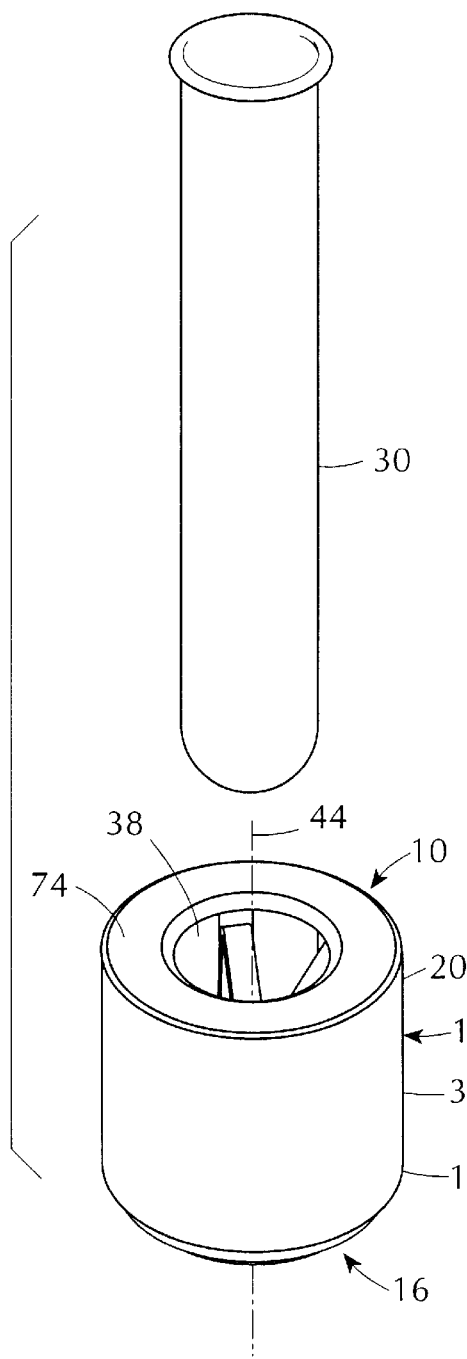
FIG. 1 is a simplified perspective view of a puck incorporating the present invention, prior to receiving a sample tube.

A puck incorporating one embodiment of the invention is generally indicated by the reference number 10.

Referring to FIGS. 2 and 6, the puck 10 includes a generally cylindrical housing 12, a spring device 14 disposed in the housing and an end cap 16 provided at a lower end 18 of the housing. An opposite upper end 20 of the housing has a tube receiving opening 22 that provides access to an interior space 26 of the housing which accommodates a sample tube 30.

Figure 4:
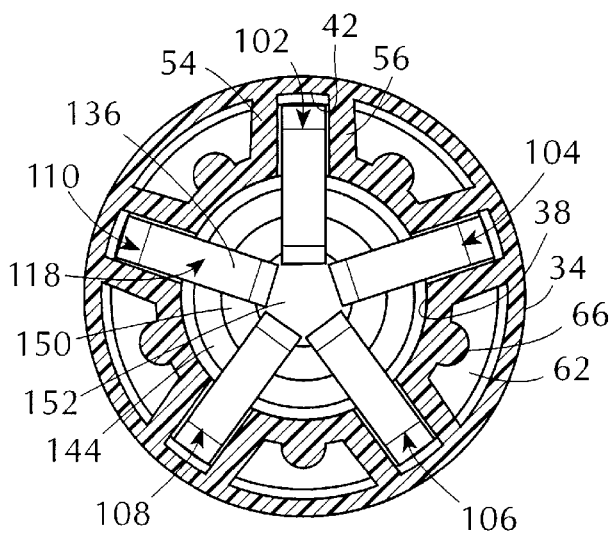
FIG. 4 is a sectional view taken on the line 4—4 of FIG. 2.
Figure 5:
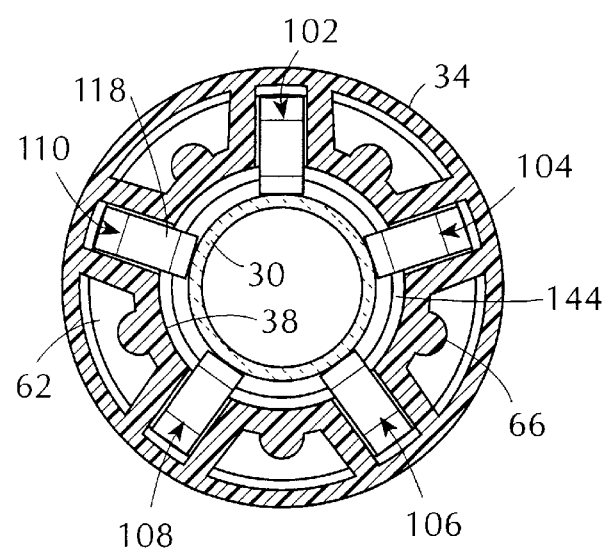
FIG. 5 is a sectional view thereof taken on the line 5—5 of FIG. 3.

The housing 12 is formed of plastic, preferably an acetal resin, having an outside cylindrical wall 34 extending from the lower housing end 18 to the upper housing end 20. The housing 12 further includes an inner wall portion 38 spaced from the cylindrical wall 34 (FIG. 4). The inner wall portion 38 defines the interior space 26 of the housing and contains five slots 42, equally spaced approximately 72 degrees around a central axis 44 (FIG. 1) of the housing 12. The slots 42 have a radial extent from the inner wall portion 38 to the cylindrical wall 34 and a length that runs from slightly within the lower housing end 18 to the upper housing end 20. The slots 42 are open at the lower housing end 18 as indicated by reference number 46 (FIG. 6) and have slot side walls 54 and 56.

Hollow spaces 62 (FIG. 4) between the inner wall portion 38 and the cylindrical wall 34 are open at the housing end 18. The housing 12 is preferably molded and ejector pin pads 66 are preferably provided in the hollow spaces 62 on the inside of the inner wall portion 38 (FIG. 4).

The cylindrical wall 34 extends slightly beyond the open ends of the slots 42 and the hollow spaces 62 at the lower housing end 18 as indicated by the reference number 68 (FIG. 6). An upper annular base portion 74 at the upper housing end 20 closes off the slots 42 and the hollow spaces 62. The upper annular base portion 74 has an inner circumferential edge 76 of slightly smaller diameter than the diameter of the inner wall portion 38 so as to define a small ledge 78. The ledge 78 helps to keep an inserted sample tube 30 away from the inner wall portion 38 as the sample tube enters the tube receiving opening 22 of the housing 12.

The spring device 14 is preferably formed of metal such as stainless steel and can be stamped as a one-piece flat structure as shown in FIG. 8 and then bent to the desired form. The spring device 14 in blank form is preferably approximately 0.007 inches thick and has an annular base portion 100. Equally spaced spring arms 102, 104, 106, 108 and 110 extend upwardly from an outer peripheral edge 112 of the annular base portion 100. The spring arms 102–110 each include a radially outer section 116 (FIG. 6) and a radially inner section 118 joined by a bent over portion 120.

The radially outer section 116 has a bottom end 124 at the annular base 100 and an intermediate bend 126 between the bottom end 124 and the bent over portion 120. The radially outer section is considered to extend from the bottom end 124 to the bent over portion 120.

The radially inner section 118 of the spring arms 102–110 has a downwardly directed free end 130 extended toward the annular base 100 and an intermediate bend 132 between the free end 130 and the bent over portion 120. A sample tube engaging portion 136 of the radially inner section 118 between the intermediate bend 132 and the free end 130 is substantially parallel to the central axis 44 of the housing 12 as most clearly shown in FIG. 2. The free end 130 is bent slightly away from the central axis 44 of the housing 12 toward the radially outer section 116. The radially inner section is considered to extend from the bent over portion 120 to the free end 130.

The end cap 16 (FIG. 6) which is preferably formed of metal such as stainless steel includes a base portion 140 with an upwardly projecting hub 144. The hub 144 includes peripheral groove 146 and a reduced diameter hub extension 148 with a rounded concave surface 150. The top edge of the hub 144 is chamfered to provide an edge 147 at the peripheral groove 146. A central opening 152 is formed in the base portion 140 and extends through the rounded concave surface 150.

Assembly of the puck 10 includes locating the annular base 100 of the spring device 14 around the hub 144 of the end cap 16 to form a subassembly 160 as shown in FIG. 7. The subassembly 160 is inserted into the lower end 18 of the housing 12.

It will be noted that the inner diameter 114 (FIG. 8) of the annular base portion 100 of the spring device 14 is sized to snugly fit around the end cap hub 144. The subassembly 160 of the spring device 14 and the end cap 16 is then directed into the lower housing end 18 such that the spring arms 102–110 align with and are received in the slots 42 until the annular base 100 of the spring device 14 bottoms against the ends of the inner wall 38 at the lower housing end 18 as shown in FIGS. 2 and 3.

The periphery of the hub 144 is sized to closely engage the inner wall portion 38 of the housing 12 such that the edge 147 presses against the inner wall 38 to provide a press fit of the end cap 16 in the housing 12. If desired bonding material can also be provided at the annular base 100 of the spring and in the peripheral groove 146. Under this arrangement the intermediate bend 126 of the radially outer section 116 of the spring arms 102–110 engage the cylindrical wall 34 within the confines of the slots 42. The radially inner sections 118 of the spring arms 102–110 are disposed in the interior space 26 of the housing 12. The portions 136 of the radially inner sections 118 are substantially parallel to the central axis 44 of the housing 12, which is also the central axis of the puck 10.

A sample tube 30 disposed in the puck 10 in the manner shown in FIGS. 1 and 3 bottoms against the rounded convex surface 150 of the cap 16 and the wall of the sample tube 30 is contacted by the sample tube engaging portions 136 of the spring arms 102–110. Insertion of the sample tube 30 causes the spring arm portions 136 to deflect away from the central axis 44 while the bend portions 126 of each spring arm 102–110 remains in fixed position against the cylindrical wall 34 within the slots 42. The spring arms 102–110 thus exert an optimum biasing or restraining force on the periphery of the sample tube 30 that retains the sample tube 30 within the housing 12 yet permits easy withdrawal of the sample tube 30 from the housing 12 when such removal is desired.

In this manner, the puck 10 serves as a carrier for the sample tube 30 when the puck 10 is disposed on a conveyor. The end cap 16 provides the puck 10 with sufficient weight to help the puck 10 remain stable on the conveyor while the puck 10 is being transported from one location to another.

Although the bend angles and size of the spring device 14 and the housing 12 are a matter of choice depending upon the diameter of the sample tube 30 the following magnitudes have been found to provide an optimum retaining force on a sample tube 30 in the diametrical range of approximately 13 mm to 16 mm and a height range of approximately 75 mm to 100 mm.

The spring arms 102–110 are preferably approximately ⅛ inch wide and have a height of approximately ¹⁵⁄₁₆ inches from the annular base 100 to the bent over portion 120. The intermediate bend 126 is formed approximately ½ inch from the annular base 100. The portion of the radially outer section 116 between the annular base 100 and the intermediate bend 126 is inclined at an angle of approximately 9 degrees away from the vertical toward the cylindrical wall 34 of the housing 12.

The portion of the radially outer section 116 between the intermediate bend 126 and the bent over portion 120 is inclined approximately 9 degrees toward the central axis 44 of the cylindrical housing 12. The portion of the radially inner section 118 between the bent over portion 120 and the intermediate bend 132 is inclined approximately 45 degrees with respect to the vertical and the portion of the radially inner section 118 between the intermediate bend 132 and the free end 130 is inclined toward the central axis of the cylindrical housing 12 by an angle of approximately 5 degrees. The distance between the intermediate bend 132 and the free end 130 is approximately ⁵⁄₁₆ inches and the distance of the free end 130 from the annular base 100 is approximately ⁷⁄₁₆ inches. The annular base 100 has an inner diameter of approximately ⅝ inches and an outer diameter of approximately 1 inch.

The inner diameter of the housing 12 at the cylindrical wall 34 is approximately 1⅛ inches and the slots 42–50 are approximately ⁵⁄₃₂ inches wide. The inner diameter of the housing at the inner wall portion 38 is approximately ¹¹⁄₁₆ inches. The housing is approximately 1³⁄₃₂ inches in height and has an outside diameter of approximately 1⁷⁄₃₂ inches.

Some advantages of the invention evident from the foregoing description include a puck that contains a one piece spring device that centers and retains a sample tube within the puck interior, a puck that is easy to assemble from three basic component parts that include the housing, the spring device and the end cap, a puck that is capable of retaining sample tubes of different diameters within a predetermined diametrical range and a puck which permits easy release and insertion of sample tubes.

In view of the above, it will be seen that the several objects of the invention are achieved and other advantageous results attained.

As various changes can be made in the above constructions without departing from the scope of the invention, it is intended that all matter contained in the above description or shown in the accompanying drawings shall be interpreted as illustrative and not in a limiting sense.

What is claimed is:

1. A puck comprising,
   a) a generally cylindrical housing having a central axis and a tube receiving opening at one end of the housing to provide access to an interior space of the housing and an end cap at the opposite end of the housing, and
   b) a spring supported on said end cap and having a plurality of spring arms projecting upwardly from said end cap toward the tube receiving opening, said spring arms being angularly spaced around the interior space of said housing.

2. The puck as claimed in claim 1 wherein said spring arms include a radially outer section with respect to said central axis, and a radially inner section with respect to said central axis, said radially inner and outer sections being joined by a bent over portion of said spring arms.

3. The puck as claimed in claim 2 wherein said radially inner section includes a free end directed downwardly toward said end cap.

4. The puck as claimed in claim 3 wherein said housing includes an inner wall portion, the radially outer section of said spring arm being recessed in said inner wall portion and the radially inner section of said spring arm extending within the interior space of said housing.

5. The puck as claimed in claim 4 wherein said housing includes an inside wall surface recessed from said inner wall portion, said radially outer section being biased against said inside wall surface.

6. The puck as claimed in claim 5 wherein the housing has an outer wall portion spaced from the inner wall portion and the outer wall portion includes said inside wall surface.

7. The puck as claimed in claim 5 wherein said radially outer section of said spring arms have a fixed bottom end and extend from said fixed bottom end to said bent over portion, said radially outer section of said spring arms further including a first intermediate bend between said fixed bottom end and said bent over portion, and said radially outer section of said spring arms being biased against said inside wall surface at said intermediate bend.

8. The puck as claimed in claim 2 wherein said radially outer section includes a fixed bottom end and extends to said bent over portion, with a first intermediate bend between said fixed bottom end and said bent over portion.

9. The puck as claimed in claim 8 wherein said radially inner section of said spring arm has a free end directed downwardly toward said end cap, said radially inner section extending from said bent over portion to said free end.

10. The puck as claimed in claim 9 wherein said radially inner section has a second intermediate bend between said bent over portion and said free end.

11. The puck as claimed in claim 10 wherein a portion of the radially inner section of said spring arms between said second intermediate bend and said free end is substantially parallel to the axis of said housing to engage a sample tube disposed in said puck.

12. The puck as claimed in claim 1 wherein said spring is formed in one piece separately of said housing and said end cap.

13. The puck as claimed in claim 12 wherein said spring includes a circular base portion and said spring arms extend upwardly from said circular base portion.

14. The puck as claimed in claim 13 wherein said circular base portion has an outer periphery and said spring arms extend upwardly from the outer periphery of said circular base portion.

15. The puck as claimed in claim 13 wherein said circular base portion is annular.

16. The puck as claimed in claim 1 wherein said housing includes an inner wall portion defining the interior space of said housing and a predetermined number of slots in said inner wall portion.

17. The puck as claimed in claim 16 wherein said housing includes an outer wall and said inner wall is spaced from said outer wall such that said slots have a radial depth at said outer wall.

18. The puck as claimed in claim 1 wherein said end cap includes a central opening.

19. The puck as claimed in claim 1 wherein said end cap includes a hub portion projecting into the interior space of said housing for press fitting engagement with said housing.

20. The puck as claimed in claim 19 wherein said spring device includes an annular base portion sized to fit around said hub portion.

21. A puck comprising,
   a) a generally cylindrical housing having a central axis and a tube receiving opening at one end of the housing to provide access to an interior space of the housing and an end cap at the opposite end of the housing, and b) a one-piece spring joined to said end cap away from the cylindrical housing and having a plurality of spring arms projecting upwardly from said end cap against said cylindrical housing and toward the tube receiving opening, said spring arms being angularly spaced around the interior space of said housing.

* * * * *